United States Patent [19]

Paradissis et al.

[11] Patent Number: 5,494,678
[45] Date of Patent: Feb. 27, 1996

[54] MULTI-VITAMIN AND MINERAL SUPPLEMENT FOR PREGNANT WOMEN

[75] Inventors: George Paradissis, St. Louis; R. Saul Levinson; Gary Heeter, both of Chesterfield, all of Mo.; Robert Cuca, Edwardsville, Ill.; Mitchell I. Kirschner, St. Louis, Mo.

[73] Assignee: KV Pharmaceutical Corporation, St. Louis, Mo.

[21] Appl. No.: 410,733

[22] Filed: Mar. 27, 1995

Related U.S. Application Data

[63] Continuation of Ser. No. 949,213, Sep. 23, 1992, abandoned.
[51] Int. Cl.$^6$ .................................................. A61K 31/00
[52] U.S. Cl. ........................ 424/439; 424/442; 514/904; 514/905
[58] Field of Search .................................. 424/439, 442; 426/72, 74; 514/904, 905

[56] References Cited

U.S. PATENT DOCUMENTS

| | | | |
|---|---|---|---|
| 4,431,634 | 2/1984 | Ellenbogen | 424/648 |
| 4,629,625 | 12/1986 | Gaull | 424/643 |
| 4,710,387 | 12/1987 | Uiterwaal et al. | 426/72 |
| 4,752,479 | 6/1988 | Briggs et al. | 424/472 |
| 4,931,441 | 6/1990 | Lawrence | 514/249 |
| 4,945,083 | 7/1990 | Jansen, Jr. | 514/52 |
| 4,994,283 | 2/1991 | Mehansho et al. | 426/74 |

OTHER PUBLICATIONS

A. T. Diplock, "Antioxidant Nutrients and Disease Prevention: An Overview,"189S–193S, *Am. J. Clin. Nutr.*, 53 (1991).
*Documenta Ceigy*, 7th Ed., (Diem, K. and Cemtuer, eds.), 457–497, Diba–Geigy Ltd., Ardsley, NY, (1975).
*Maternal Nutrition and the Course of Pregnancy, Summary Report*, 23, Appendix C, Committee on Maternal Nutrition/ Food and Nutrition Board, National Research Council, National Academy of Sciences, U.S. Govt. Printing Office, Washington, D.C. (1970).
Whitehead, R. G., "Pregnancy and Lactation", in *Modern Nutrition in Health and Disease*, 7th Ed., (Shils, M. E. and Young, V. R. eds.), 934, Lea & Febigers, Philadelphia (1988).
Rosso, P., ed. "Maternal Metabolism of Vitamins and Minerals," in *Nutrition and Metabolism in Pregnancy: Mother and Fetus*, 81–101, 118–132, Oxford Press (1990).
Hallberg, L., "Iron Balance in Pregnancy", in *Vitamins and Minerals in Pregnancy and Lactation*, (Berger, H., ed.), 115–127, Raven Press, New York (1988).
Glorieux, F. H. et al., "Calcium and Vitamin D, Status During Pregnancy," in *Vitamins and Minerals Pregnancy and Lactation*, 135–143, (Berger, H., ed.), Raven Press, New York (1988).
Worthington–Roberts, V. et al., "Physiological Basis of Nutritional Needs" in *Nutrition in Pregnancy and Lactation*, 3rd Ed., 73–78, 120–131, Time Mirror/Mosby College Publishing (1985).
Chanarin, I., "Folate," in *Vitamins and Minerals in Pregnancy and Lactation Berger, H., ed.)*, 129–134, Raven Press, New York (1988).
Schorah, C., "Importance of Adequate Folae Nutrition in Embryonic and Early Fetal Development," in *Vitamins and Minerals in pregnancy and Lactation*, (Berger, H., ed.), 167–176, Raven Press, New York (1988).
Facsimile transmission from Mr. Suzanne Gaby to Gary Heeter, (Jan. 20, 1992) (information relating to vitamin and iron absorption).
Highest 1989 RDA, Current U.S. RDA and Proposed RDI for Vitamins and Minerals, (chart prepared from Part III, FDA Proposed Rules for Food Labeling Reference Daily Intakes, Fed. Reg. 29476–29533, Jul. 19, 1990.

*Primary Examiner*—Melvyn I. Marquis
*Assistant Examiner*—Robert H. Harrison
*Attorney, Agent, or Firm*—Nath & Associates; Gary M. Nath; Suet M. Chong

[57] ABSTRACT

Multi-vitamin and mineral supplements for administration to a pregnant woman during her first, second, and third trimesters of pregnancy comprising specific regimens of a pharmaceutically acceptable calcium compound, vitamin D, folic acid, vitamin $B_{12}$, vitamin $B_6$, and vitamin $B_1$. The prenatal supplements are specifically tailored to maximize fetal development and maternal health during each trimester of pregnancy.

3 Claims, No Drawings

MULTI-VITAMIN AND MINERAL SUPPLEMENT FOR PREGNANT WOMEN

This application is a continuation application of U.S. patent application Ser. No. 07/949,213, filed Sep. 23, 1992, now abandoned, the entire application of which hereby incorporated in their entirety.

BACKGROUND OF THE INVENTION

1. Field of the Invention

The present invention relates to multi-vitamin and mineral supplements, and particularly to a novel multi-vitamin and mineral supplement for administration during pregnancy.

2. Description of Related Art

Vitamin and mineral preparations are commonly administered to treat specific medical conditions or as general nutritional supplements. Recent studies have elucidated the important physiological roles played by vitamins and minerals, and established a correlation between deficiencies or excesses of these nutrients and the etiologies of certain disease states in humans. See, e.g., Diplock, "Antioxidant Nutrients and Disease Prevention: An Overview," *Am. J. Clin. Nutr.*, 53:189–193 (1991); *Documenta Geigy Scientific Tables*, 457–497, (Diem and Cemtuer eds., 7th ed., 1975).

It has further become recognized that various, groups of the human population require different quantities and types of vitamins and minerals to prevent or alleviate diseases, as well as to maintain general good health. For example, it is known that pregnant women commonly require iron therapy to prevent or treat iron-deficiency anemia. Various prior patents have been directed to improving the efficacy of iron supplements for use during pregnancy. U.S. Pat. No. 4,994,283, for example, discloses nutritional mineral supplements which include iron and calcium compounds in combination with citrates or tartrates, ascorbates, and fructose. The tendency of calcium to inhibit the bioavailability of iron is said to be reduced in such compositions, so that the conjoint bioavailability of these two minerals is enhanced.

U.S. Pat. No. 4,431,634 maximizes the bioavailability of iron in prenatal iron supplements by maintaining the amount of calcium compounds in the supplement at 300 mg or less and the amount of magnesium compounds at 75 mg or less per dosage unit.

Another approach to the same problem is found in U.S. Pat. No. 4,752,479, wherein a multi-vitamin and mineral dietary supplement is provided which includes (a) one or more divalent dietary mineral components such as calcium or magnesium; and (b) a bioavailable iron component, present in a controlled release form and adapted to be released in a controlled manner in the gastrointestinal tract.

U.S. Pat. No. 4,710,387 discloses a nutritional supplement preparation for pregnant and breast-feeding women which contains 10–20% by weight of protein, 16–28% by weight of fat, 43–65% by weight carbohydrates, and at most 3.5% by weight of moisture, minerals, trace elements and vitamins.

Despite the foregoing efforts to improve vitamin and mineral supplementation for pregnant women, conventional prenatal supplements exhibit several deficiencies. One notable problem is that currently available prenatal vitamins are unitary formulations which do not differentiate the presence and levels of particular nutritional components depending upon the stage of fetal development. Such unitary formulations are wasteful of nutritional materials, and do not take into account the significant variations in the nutritional requirements for both the mother and the developing fetus depending upon the stage of fetal development.

Thus, conventional prenatal supplements typically provide inadequate levels of calcium and other essential nutrients during the third trimester of fetal development when such nutrients are most needed, and may provide excessive levels of other nutrients during the first and second trimesters when such dosage levels are unneeded and perhaps even harmful. For example, the excessive presence of iron in conventional prenatal supplements often produces stomach upset in the mother during the first trimester of fetal growth, when morning sickness is most pronounced.

It would therefore be desirable to provide a prenatal multi-vitamin and mineral supplement which overcomes the aforementioned deficiencies of the prior art.

SUMMARY OF THE INVENTION

The present invention overcomes the shortcomings of known unitary prenatal supplements by providing multi-vitamin and mineral supplements which are specifically tailored for administration during the first, second, and third trimesters of pregnancy. The formulations of the invention have been found to maximize the benefit of vitamin and mineral supplementation both for the developing fetus and the mother, while concurrently minimizing the undesirable side effects characteristic of known prenatal nutritional supplements.

The compositions of the invention include certain essential nutritional components in dosage levels which have been found to optimize fetal development and maintain the mother's health during each of the trimesters of pregnancy.

Thus, the invention provides a multi-vitamin and mineral supplement for administration to a pregnant woman during her first trimester of pregnancy, which comprises:

(a) from about 200 mg to about 300 mg of elemental calcium, dosed in the form of a pharmaceutically acceptable calcium compound;

(b) from about 350 I.U. to about 450 I.U. of vitamin D;

(c) from about 0.5 mg to about 1.5 mg of folic acid;

(d) from about 5 mcg to about 10 mcg of vitamin $B_{12}$;

(e) from about 12 mg to about 20 mg of vitamin $B_6$; and (f) from about 1.0 mg to about 2.0 mg of vitamin $B_1$.

A multi-vitamin and mineral supplement for administration to a pregnant woman during her second trimester of pregnancy is provided, which comprises:

(a) from about 275 mg to about 375 mg of elemental calcium, dosed in the form of a pharmaceutically acceptable calcium compound;

(b) from about 400 I.U. to about 500 I.U. of vitamin D;

(c) from about 0.5 mg to about 1.5 mg of folic acid;

(d) from about 7 mcg to about 12 mcg of vitamin $B_{12}$;

(e) from about 14 mg to about 22 mg of vitamin $B_6$; and (f) from about 1.1 mg to about 2.1 mg of vitamin $B_1$.

A multi-vitamin and mineral supplement for administration to a pregnant woman during her third trimester of pregnancy is also provided by the invention, wherein the formulation comprises:

(a) from about 450 mg to about 550 mg of elemental calcium, dosed in the form of a pharmaceutically acceptable calcium compound;

(b) from about 450 I.U. to about 550 I.U. of vitamin D;

(c) from about 0.5 mg to about 1.5 mg of folic acid;
(d) from about 9 mcg to about 14 mcg of vitamin $B_{12}$;
(e) from about 16 mg to about 24 mg of vitamin $B_6$; and
(f) from about 1.2 mg to about 2.2 mg of vitamin $B_1$.

Each of the above prenatal nutritional formulations may be administered in any conventional pharmaceutical delivery system, with or without additional nutritional components as described in further detail below.

If desired, the products of the invention may be conveniently marketed as a prenatal multi-vitamin and mineral system which comprises the three distinct multi-vitamin and mineral supplements described above. The prenatal multi-vitamin and mineral system contemplated by the invention includes means for permitting the pregnant woman to differentiate between the formulations for administration during the first, second, and third trimesters.

DESCRIPTION OF THE PREFERRED EMBODIMENTS

The invention is based on the discovery that prenatal multi-vitamin and mineral supplements can be provided which are specifically tailored for administration during each of the trimesters of pregnancy. The products of the invention provide optimum nutritional components and amounts which have been found to benefit fetal growth and the mother's health throughout pregnancy, while concurrently minimizing the undesired side effects of conventional unitary formulations.

According to a first aspect of the invention, a multi-vitamin and mineral supplement for administration to a pregnant woman during her first trimester of pregnancy is provided, which comprises:

(a) from about 200 mg to about 300 mg of elemental calcium, dosed in the form of a pharmaceutically acceptable calcium compound;
(b) from about 350 I.U. to about 450 I.U. of vitamin D;
(c) from about 0.5 mg to about 1.5 mg of folic acid;
(d) from about 5 mcg to about 10 mcg of vitamin $B_{12}$;
(e) from about 12 mg to about 20 mg of vitamin $B_6$; and
(f) from about 1.0 mg to about 2.0 mg of vitamin $B_1$.

A preferred embodiment of the first trimester formulation includes:

(a) from about 225 mg to about 275 mg of elemental calcium, dosed in the form of a pharmaceutically acceptable calcium compound;
(b) from about 375 I.U. to about 425 I.U. of vitamin D;
(c) from about 0.75 mg to about 1.25 mg of folic acid;
(d) from about 7 mcg to about 9 mcg of vitamin $B_{12}$;
(e) from about 14 mg to about 18 mg of vitamin $B_6$; and
(f) from about 1.3 mg to about 1.7 mg of vitamin $B_1$.

Useful pharmaceutically acceptable calcium compounds include any of the well-known calcium supplements, such as calcium carbonate, calcium sulfate, calcium oxide, calcium hydroxide, calcium apatite, calcium citrate-malate, bone meal, oyster shell, calcium gluconate, calcium lactate, calcium phosphate, calcium levulinate, and the like. Preferably, calcium compounds selected from the group consisting of calcium carbonate, calcium sulfate, and mixtures thereof are employed.

The first trimester multi-vitamin and mineral supplement of the invention may include additional nutritional components well-known in the art. For example, the supplement may include from about 10 mg to about 40 mg of elemental magnesium, in the form of one or more pharmaceutically acceptable magnesium compounds, such as magnesium stearate, magnesium carbonate, magnesium oxide, magnesium hydroxide, and magnesium sulfate. Magnesium stearate is preferred.

In a preferred embodiment, the multi-vitamin and mineral supplement for administration during the first trimester comprises:

(a) from about 225 mg to about 275 mg of elemental calcium, dosed in the form of a pharmaceutically acceptable calcium compound;
(b) from about 375 I.U. to about 425 I.U. of vitamin D;
(c) from about 0.75 mg to about 1.25 mg of folic acid;
(d) from about 7 mcg to about 9 mcg of vitamin $B_{12}$;
(e) from about 14 mg to about 18 mg of vitamin $B_6$;
(f) from about 1.3 mg to about 1.7 mg of vitamin $B_1$;
(g) from about 0 I.U. to about 4500 I.U. of beta carotene;
(h) from about 0 mg to about 30 mg of vitamin E;
(i) from about 0 mg to about 3.7 mg of vitamin $B_2$;
(j) from about 0 mg to about 20 mg of vitamin $B_3$;
(k) from about 0 mg to about 100 mg of vitamin C;
(l) from about 0 mg to about 80 mg of elemental iron, dosed in the form of a pharmaceutically acceptable iron compound;
(m) from about 0 mg to about 3 mg of elemental copper, dosed in the form of a pharmaceutically acceptable copper compound;
(n) from about 0 mg to about 0.2 mg of elemental iodine, dosed in the form of a pharmaceutically acceptable iodine compound;
(o) from about 0 mg to about 25 mg of elemental zinc, dosed in the form of a pharmaceutically acceptable zinc compound; and
(p) from about 0 mg to about 40 mg of elemental magnesium, dosed in the form of a pharmaceutically acceptable magnesium compound.

More preferably, the multi-vitamin and mineral supplement for administration during the first trimester comprises:

(a) from about 225 mg to about 275 mg of elemental calcium, dosed in the form of a pharmaceutically acceptable calcium compound;
(b) from about 375 I.U. to about 425 I.U. of vitamin D;
(c) from about 0.75 mg to about 1.25 mg of folic acid;
(d) from about 7 mcg to about 9 mcg of vitamin $B_{12}$;
(e) from about 14 mg to about 18 mg of vitamin $B_6$;
(f) from about 1.3 mg to about 1.7 mg of vitamin $B_1$;
(g) from about 3500 I.U. to about 4500 I.U. of beta carotene;
(h) from about 20 mg to about 30 mg of vitamin E;
(i) from about 3 mg to about 3.7 mg of vitamin $B_2$;
(j) from about 10 mg to about 20 mg of vitamin $B_3$;
(k) from about 60 mg to about 100 mg of vitamin C;
(l) from about 50 mg to about 80 mg of elemental iron, dosed in the form of a pharmaceutically acceptable iron compound;
(m) from about 1 mg to about 3 mg of elemental copper, dosed in the form of a pharmaceutically acceptable copper compound;
(n) from about 0.05 mg to about 0.2 mg of elemental iodine, dosed in the form of a pharmaceutically acceptable iodine compound;

(o) from about 15 mg to about 25 mg of elemental zinc, dosed in the form of a pharmaceutically acceptable zinc compound; and (p) from about 20 mg to about 30 mg of elemental magnesium, dosed in the form of a pharmaceutically acceptable magnesium compound.

When a prenatal supplement having additional nutritional components is provided as described above, the pharmaceutically acceptable iron compound may be chosen from any of the well-known iron II (ferrous) or iron III (ferric) supplements, such as ferrous sulfate, ferric chloride, ferrous gluconate, ferrous lactate, ferrous tartrate, iron-sugar-carboxylate complexes, ferrous fumarate, ferrous succinate, ferrous glutamate, ferrous citrate, ferrous pyrophosphate, ferrous cholinisocitrate, ferrous carbonate, and the like.

Preferably, the iron compound comprises a pharmaceutically acceptable ferrous sulfate compound coated with a pharmaceutically acceptable film forming material which permits release of the ferrous sulfate in the intestine of a woman administered the supplement. Suitable coatings include any material known in the art for forming enteric, controlled release, or sustained release coatings, such as cellulose ethers including hydroxypropyl methylcellulose, methylcellulose, ethylcellulose, and carboxymethylcellulose; cellulose esters such as cellulose acetate, cellulose acetate phthalate, and cellulose nitrate; acrylate and methacrylate copolymers; and the like. The coated iron compound has been found to provide increased iron bioavailability by minimizing interaction between the iron compound and divalent cations such as calcium in the prenatal supplement. As iron is believed to be a cause of morning sickness, release of the iron in the intestine also minimizes stomach upset.

In a preferred embodiment of the first trimester formulation, the vitamin C and folic acid nutritional components are also coated to provide controlled release.

The first trimester multi-vitamin and mineral supplement may contain a pharmaceutically acceptable copper compound in the form of cupric oxide, cupric sulfate, or cupric gluconate, with cupric oxide being preferred. Preferred pharmaceutically acceptable iodine compounds include sodium or potassium iodide, with potassium iodide being most preferred. Useful pharmaceutically acceptable zinc compounds include zinc sulfate, zinc chloride, and zinc oxide, with zinc sulfate being preferred.

According to a second aspect of the invention, a multi-vitamin and mineral supplement for administration to a pregnant woman during her second trimester of pregnancy is provided, which comprises:

(a) from about 275 mg to about 375 mg of elemental calcium, dosed in the form of a pharmaceutically acceptable calcium compound;

(b) from about 400 I.U. to about 500 I.U. of vitamin D;

(c) from about 0.5 mg to about 1.5 mg of folic acid;

(d) from about 7 mcg to about 12 mcg of vitamin $B_{12}$;

(e) from about 14 mg to about 22 mg of vitamin $B_6$; and (f) from about 1.1 mg to about 2.1 mg of vitamin $B_1$.

A preferred form of this second aspect of the invention contemplates a multi-vitamin and mineral supplement for administration during the second trimester of pregnancy, which comprises:

(a) from about 300 mg to about 350 mg of elemental calcium, dosed in the form of a pharmaceutically acceptable calcium compound;

(b) from about 425 I.U. to about 475 I.U. of vitamin D;

(c) from about 0.75 mg to about 1.25 mg of folic acid;

(d) from about 9 mcg to about 11 mcg of vitamin $B_{12}$;

(e) from about 16 mg to about 11 mg of vitamin $B_6$; and (f) from about 1.4 mg to about 1.8 mg of vitamin $B_1$.

Useful pharmaceutically acceptable calcium compounds include the calcium salts listed above, again preferably selected from the group consisting of calcium carbonate, calcium sulfate, and mixtures thereof.

The second trimester formulation may similarly include other nutritional agents known in the art. For example, the invention contemplates the optional addition to the second trimester formulation of from about 35 mg to about 65 mg of elemental magnesium, in the form of a pharmaceutically acceptable magnesium compound as listed above, preferably magnesium stearate.

In a preferred embodiment of the second trimester formulation, the multi-vitamin and mineral supplement comprises:

(a) from about 300 mg to about 350 mg of elemental calcium, dosed in the form of a pharmaceutically acceptable calcium compound;

(b) from about 425 I.U. to about 475 I.U. of vitamin D;

(c) from about 0.75 mg to about 1.25 mg of folic acid;

(d) from about 9 mcg to about 11 mcg of vitamin $B_{12}$;

(e) from about 16 mg to about 20 mg of vitamin $B_6$;

(f) from about 1.4 mg to about 1.8 mg of vitamin $B_1$;

(g) from about 0 I.U. to about 5500 I.U. of beta carotene;

(h) from about 0 mg to about 35 mg of vitamin E;

(i) from about 0 mg to about 4 mg of vitamin $B_2$;

(j) from about 0 mg to about 20 mg of vitamin $B_3$;

(k) from about 0 mg to about 120 mg of vitamin C;

(l) from about 0 mg to about 100 mg of elemental iron, dosed in the form of a pharmaceutically acceptable iron compound;

(m) from about 0 mg to about 3 mg of elemental copper, dosed in the form of a pharmaceutically acceptable copper compound;

(n) from about 0 mg to about 0.2 mg of elemental iodine, dosed in the form of a pharmaceutically acceptable iodine compound;

(o) from about 0 mg to about 25 mg of elemental zinc, dosed in the form of a pharmaceutically acceptable zinc compound; and (p) from about 0 mg to about 65 mg of elemental magnesium, dosed in the form of a pharmaceutically acceptable magnesium compound.

More preferably, the second trimester formulation comprises:

(a) from about 300 mg to about 350 mg of elemental calcium, dosed in the form of a pharmaceutically acceptable calcium compound;

(b) from about 425 I.U. to about 475 I.U. of vitamin D;

(c) from about 0.75 mg to about 1.25 mg of folic acid;

(d) from about 9 mcg to about 11 mcg of vitamin $B_{12}$;

(e) from about 16 mg to about 20 mg of vitamin $B_6$;

(f) from about 1.4 mg to about 1.8 mg of vitamin $B_1$;

(g) from about 4500 I.U. to about 5500 I.U. of beta carotene;

(h) from about 25 mg to about 35 mg of vitamin E;

(i) from about 3.3 mg to about 4 mg of vitamin $B_2$;

(j) from about 14 mg to about 22 mg of vitamin $B_3$;

(k) from about 80 mg to about 120 mg of vitamin C;

(l) from about 65 mg to about 95 mg of elemental iron, dosed in the form of a pharmaceutically acceptable iron compound;

(m) from about 1 mg to about 3 mg of elemental copper, dosed in the form of a pharmaceutically acceptable copper compound;

(n) from about 0.05 mg to about 0.2 mg of elemental iodine, dosed in the form of a pharmaceutically acceptable iodine compound;

(o) from about 15 mg to about 25 mg of elemental zinc, dosed in the form of a pharmaceutically acceptable zinc compound; and 1(p) from about 45 mg to about 55 mg of elemental magnesium, dosed in the form of a pharmaceutically acceptable magnesium compound.

Preferred pharmaceutically acceptable compounds are the same as described above with respect to the first trimester formulation. Also, the iron, vitamin C, and folic acid components are again preferably provided with a controlled release coating.

A multi-vitamin and mineral supplement for administration to a pregnant woman during her third trimester of pregnancy is provided by the invention, which comprises:

(a) from about 450 mg to about 550 mg of elemental calcium, dosed in the form of a pharmaceutically acceptable calcium compound;

(b) from about 450 I.U. to about 550 I.U. of vitamin D;

(c) from about 0.5 mg to about 1.5 mg of folic acid;

(d) from about 9 mcg to about 14 mcg of vitamin $B_{12}$;

(e) from about 16 mg to about 24 mg of vitamin $B_6$; and (f) from about 1.2 mg to about 2.2 mg of vitamin $B_1$.

A preferred form of the third trimester composition comprises:

(a) from about 475 mg to about 525 mg of elemental calcium, dosed in the form of a pharmaceutically acceptable calcium compound;

(b) from about 475 I.U. to about 525 I.U. of vitamin D;

(c) from about 0.75 mg to about 1.25 mg of folic acid;

(d) from about 11 mcg to about 13 mcg of vitamin $B_{12}$;

(e) from about 18 mg to about 22 mg of vitamin $B_6$; and (f) from about 1.5 mg to about 1.9 mg of vitamin $B_1$.

Pharmaceutically acceptable calcium compounds include those salts enumerated above, again preferably selected from the group consisting of calcium carbonate, calcium sulfate, and mixtures thereof.

The third trimester multi-vitamin and mineral supplement may further include from about 85 mg to about 115 mg of elemental magnesium, in the form of a pharmaceutically acceptable magnesium compound, preferably magnesium stearate. Other supplemental nutritional components may also be added to the third trimester formulation. In this regard, the multi-vitamin and mineral supplement for administration during the third trimester of pregnancy may comprise:

(a) from about 475 mg to about 525 mg of elemental calcium, dosed in the form of a pharmaceutically acceptable calcium compound;

(b) from about 475 I.U. to about 525 I.U. of vitamin D;

(c) from about 0.75 mg to about 1.25 mg of folic acid;

(d) from about 11 mcg to about 13 mcg of vitamin $B_{12}$;

(e) from about 18 mg to about 22 mg of vitamin $B_6$;

(f) from about 1.5 mg to about 1.9 mg of vitamin $B_1$;

(g) from about 0 I.U. to about 6500 I.U. of beta carotene;

(h) from about 0 mg to about 40 mg of vitamin E;

(i) from about 0 mg to about 4.3 mg of vitamin $B_2$;

(j) from about 0 mg to about 22 mg of vitamin $B_3$;

(k) from about 0 mg to about 140 mg of vitamin C;

(l) from about 0 mg to about 120 mg of elemental iron, dosed in the form of a pharmaceutically acceptable iron compound;

(m) from about 0 mg to about 3 mg of elemental copper, dosed in the form of a pharmaceutically acceptable copper compound;

(n) from about 0 mg to about 0.2 mg of elemental iodine, dosed in the form of a pharmaceutically acceptable iodine compound;

(o) from about 0 mg to about 25 mg of elemental zinc, dosed in the form of a pharmaceutically acceptable zinc compound; and (p) from about 0 mg to about 115 mg of elemental magnesium, dosed in the form of a pharmaceutically acceptable magnesium compound.

More preferably, the third trimester multi-vitamin and mineral supplement comprises:

(a) from about 475 mg to about 525 mg of elemental calcium, dosed in the form of a pharmaceutically acceptable calcium compound;

(b) from about 475 I.U. to about 525 I.U. of vitamin D;

(c) from about 0.75 mg to about 1.25 mg of folic acid;

(d) from about 11 mcg to about 13 mcg of vitamin $B_{12}$;

(e) from about 18 mg to about 22 mg of vitamin $B_6$;

(f) from about 1.5 mg to about 1.9 mg of vitamin $B_1$;

(g) from about 5500 I.U. to about 6500 I.U. of beta carotene;

(h) from about 30 mg to about 40 mg of vitamin E;

(i) from about 3.6 mg to about 4.3 mg of vitamin $B_2$;

(j) from about 16 mg to about 24 mg of vitamin $B_3$;

(k) from about 100 mg to about 140 mg of vitamin C;

(l) from about 85 mg to about 115 mg of elemental iron, dosed in the form of a pharmaceutically acceptable iron compound;

(m) from about 1 mg to about 3 mg of elemental copper, dosed in the form of a pharmaceutically acceptable copper compound;

(n) from about 0.05 mg to about 0.2 mg of elemental iodine, dosed in the form of a pharmaceutically acceptable iodine compound;

(o) from about 15 mg to about 25 mg of elemental zinc, dosed in the form of a pharmaceutically acceptable zinc compound; and (p) from about 95 mg to about 105 mg of elemental magnesium, dosed in the form of a pharmaceutically acceptable magnesium compound.

Preferred pharmaceutically acceptable compounds are the same as described above with respect to the first trimester composition. Again, the iron, vitamin C, and folic acid components are preferably coated with a suitable controlled release film forming material.

The third trimester formulation may optionally be provided in multiple dosage units, to facilitate administration of the increased levels of nutrients.

As previously indicated, the multi-vitamin and mineral supplements of the invention may be provided as an overall nutritional system for administration to a pregnant woman, wherein the system comprises:

(a) a multi-vitamin and mineral supplement for administration to a pregnant woman during her first trimester of pregnancy, which comprises:

(i) from about 200 mg to about 300 mg of elemental calcium, dosed in the form of a pharmaceutically acceptable calcium compound;

(ii) from about 350 I.U. to about 450 I.U. of vitamin D;
(iii) from about 0.5 mg to about 1.5 mg of folic acid;
(iv) from about 5 mcg to about 10 mcg of vitamin $B_{12}$;
(v) from about 12 mg to about 20 mg of vitamin $B_6$; and
(vi) from about 1.0 mg to about 2.0 mg of vitamin $B_1$;

(b) a multi-vitamin and mineral supplement for administration to a pregnant woman during her second trimester of pregnancy, which comprises:
  (i) from about 275 mg to about 375 mg of elemental calcium, dosed in the form of a pharmaceutically acceptable calcium compound;
  (ii) from about 400 I.U. to about 500 I.U. of vitamin D;
  (iii) from about 0.5 mg to about 1.5 mg of folic acid;
  (iv) from about 7 mcg to about 12 mcg of vitamin $B_{12}$;
  (v) from about 14 mg to about 22 mg of vitamin $B_6$; and
  (vi) from about 1.1 mg to about 2.1 mg of vitamin $B_1$; and (c) a multi-vitamin and mineral supplement for administration to a pregnant woman during her third trimester of pregnancy, which comprises:
  (i) from about 450 mg to about 550 mg of elemental calcium, dosed in the form of a pharmaceutically acceptable calcium compound;
  (ii) from about 450 I.U. to about 550 I.U. of vitamin D;
  (iii) from about 0.5 mg to about 1.5 mg of folic acid;
  (iv) from about 9 mcg to about 14 mcg of vitamin $B_{12}$;
  (V) from about 16 mg to about 24 mg of vitamin $B_6$;
  (vi) from about 1.2 mg to about 2.2 mg of vitamin $B_1$.

The nutritional supplements provided by the invention may therefore be marketed together as a single product, which will facilitate compliance with the administration of the proper formulation, thereby enhancing the benefits achieved by the products of the invention. The formulations for trimesters one, two, and three may be differentiated by any conventional means known in the pharmaceutical art. For example, different colored tablets may be provided; tablets may be scored with appropriate markings; and/or distinct packaging may be used to distinguish each formulation.

The nutritional supplements of the invention may be provided in any suitable dosage form known in the art. For example, the compositions may be incorporated into tablets, powders, granules, beads, chewable lozenges, capsules, liquids, or similar conventional dosage forms, using conventional equipment and techniques known in the art. Tablet dosage forms are preferred.

When preparing dosage forms incorporating the compositions of the invention, the nutritional components are normally blended with conventional excipients such as binders, including gelatin, pregelatinized starch, and the like; lubricants, such as hydrogenated vegetable oil, stearic acid, and the like; diluents, such as lactose, mannose, and sucrose; disintegrants, such as carboxymethyl cellulose and sodium starch glycolate; suspending agents, such as povidone, polyvinyl alcohol and the like; absorbents, such as silicon dioxide; preservatives, such as methylparaben, propylparaben, and sodium benzoate; surfactants, such as sodium lauryl sulfate, polysorbate 80, and the like; and colorants, such as F. D. & C dyes and lakes.

All of the products of the invention have been found to provide optimal nutritional supplementation for a developing fetus and mother during the first, second, and third trimesters of fetal development. For example, the third trimester composition includes increased amounts of calcium, which is crucial for bone development in the fetus during the third trimester. The reduced iron content of the first trimester formulation has been found to avoid stomach upset in the mother during the first trimester, unlike conventional prenatal supplements. Levels of beta carotene and vitamin D and certain of the other components are gradually increased in the first, second, and third trimester formulations, in correlation with the increasing need for these nutritional components as the pregnancy progresses. The compositions of the invention are also formulated to optimize fetal nerve tissue growth and development during the latter half of the second trimester and the third trimester.

All of the aforementioned benefits are achieved without wasting vitamin and mineral materials, as characteristic of unitary prenatal supplements of the prior art. This makes the products of the invention more cost effective than conventional prenatal supplements.

Although the products of the invention are preferably intended for administration to humans, it will be understood that the formulations may also be utilized in veterinary therapies for other animals.

The following example is given to illustrate the invention but is not deemed to be limiting thereof. All amounts specified in the application are based on milligrams unless otherwise indicated. The term "I.U." represents International Units.

EXAMPLE

Preparation of Prenatal Multi-Vitamin and Mineral Supplements

The following compositions were used to prepare multi-vitamin and mineral supplements for administration during the first, second, and third trimesters of pregnancy:

| Component | Trimester I | Trimester II | Trimester III |
|---|---|---|---|
| Beta Carotene, I.U. | 4000 | 5000 | 6000 |
| Vitamin D, I.U. | 400 | 450 | 500 |
| Vitamin E, mg | 25 | 30 | 35 |
| Vitamin $B_1$, mg | 1.5 | 1.6 | 1.7 |
| Vitamin $B_2$, mg | 3.4 | 3.7 | 4.0 |
| Vitamin $B_3$, mg | 16 | 18 | 20 |
| Vitamin $B_6$, mg | 16 | 18 | 20 |
| Vitamin $B_{12}$, mcg | 8 | 10 | 12 |
| Vitamin C, mg | 80 | 100 | 120 |
| Folic Acid, mg | 1 | 1 | 1 |
| Calcium, mg | 250 | 325 | 500 |
| Iron, mg | 65 | 80 | 100 |
| Copper, mg | 2 | 2 | 2 |
| Iodine, mg | 0.15 | 0.15 | 0.15 |
| Zinc, mg | 20 | 20 | 20 |
| Magnesium, mg | 25 | 50 | 100 |

Tablets incorporating the above formulations were prepared using conventional methods and materials known in the pharmaceutical art. The resulting prenatal supplement tablets were recovered and stored for future use.

The invention being thus described, it will be apparent that the same may be varied in many ways. Such variations are not to be regarded as a departure from the spirit and scope of the invention, and all such modifications are intended to be within the scope of the appended claims.

What is claimed is:

1. A multi-vitamin and mineral system for administration to a pregnant woman, consisting essentially of:
  (a) a multi-vitamin and mineral supplement for administration to a pregnant woman during her first trimester of pregnancy, which comprises:

(i) from about 200 mg to about 300 mg of elemental calcium, dosed in the form of a pharmaceutically acceptable calcium compound;
(ii) from about 350 I.U. to about 450 I.U. of vitamin D;
(iii) from about 0.5 mg to about 1.5 mg of folic acid;
(iv) from about 5 mcg to about 10 mcg of vitamin $B_{12}$;
(v) from about 12 mg to about 20 mg of vitamin $B_6$; and
(vi) from about 1.0 mg to about 2.0 mg of vitamin $B_1$;

(b) a multi-vitamin and mineral supplement for administration to a pregnant woman during her second trimester of pregnancy, consisting essentially of:
(i) from about 275 mg to about 375 mg of elemental calcium, dosed in the form of a pharmaceutically acceptable calcium compound;
(ii) from about 400 I.U. to about 500 I.U. of vitamin D;
(iii) from about 0.5 mg to about 1.5 mg of folic acid;
(iv) from about 7 mcg to about 12 mcg of vitamin $B_{12}$;
(v) from about 14 mg to about 22 mg of vitamin $B_6$; and
(vi) from about 1.1 mg to about 2.1 mg of vitamin $B_1$; and (c) a multi-vitamin and mineral supplement for administration to a pregnant woman during her third trimester of pregnancy, consisting essentially of:
(i) from about 450 mg to about 550 mg of elemental calcium, dosed in the form of a pharmaceutically acceptable calcium compound;
(ii) from about 450 I.U. to about 550 I.U. of vitamin D;
(iii) from about 0.5 mg to about 1.5 mg of folic acid;
(iv) from about 9 mcg to about 14 mcg of vitamin $B_{12}$;
(v) from about 16 mg to about 24 mg of vitamin $B_6$; and
(vi) from about 1.2 mg to about 2.2 mg of vitamin $B_1$.

2. A product for providing a vitamin and nutrient supplement regimen to pregnant women consisting essentially of: a first formulation comprising a first mixture of vitamins and minerals wherein the amounts of vitamins and minerals in said first mixture optimize fetal development and maintain the mother's health during the first trimester of pregnancy; a second formulation comprising a second mixture of vitamins and minerals wherein the amounts of vitamins and minerals in said second mixture optimize fetal development and maintain the mother's health during the second trimester of pregnancy; and a third formulation comprising a third mixture of vitamins and minerals wherein the amounts of vitamins and minerals in said third mixture optimize fetal development and maintain the mother's health during the third trimester of pregnancy wherein iron is present in a reduced state in the first trimester and beta carotene and vitamin D are used in increased concentrations in the second and third trimesters, and wherein calcium is present in increased concentrations in the third trimester.

3. The product of claim 2 wherein said second formulation contains more calcium, iron, magnesium, Vitamin C and Vitamin D than said first formulation, and wherein said third formulation contains more calcium, iron, magnesium, Vitamin C and Vitamin D than said second formulation.

* * * * *